US00PP08946P

United States Patent [19]

Zary

[11] Patent Number: Plant 8,946

[45] Date of Patent: Oct. 18, 1994

[54] FLORIBUNDA ROSE PLANT NAMED JACMOS

[75] Inventor: Keith W. Zary, Thousands Oaks, Calif.

[73] Assignee: Bear Creek Gardens, Inc., Medford, Oreg.

[21] Appl. No.: 150,455

[22] Filed: Nov. 9, 1993

[51] Int. Cl.[5] ..... A01H 5/00

[52] U.S. Cl. ..... Plt./24

[58] Field of Search ..... Plt. 24, 1

*Primary Examiner*—Howard J. Locker

*Attorney, Agent, or Firm*—Klarquist Sparkman Campbell Leigh & Whinston

[57] ABSTRACT

Floribunda rose plant having a profusion of glands and thorns on its stipules and peduncles; a profusion of thorns on its stems; dark green, leathery foliage; and freely produced thorn-covered hips that turn brown and scaly at maturity.

1 Drawing Sheet

The present invention relates to a new and distinct variety of rose plant of the floribunda class which was originated by me by crossing an unnamed seedling with the variety of JACjel, U.S. Plant Pat. No. 4,438.

The primary objective of this breeding was to produce a new rose variety having the moss character of the female parent along with the bright yellow flower character of the male parent. The objective was substantially achieved, along with other desirable improvements, as evidenced by the following unique combination of characteristics that are outstanding in the new variety and that distinguish it from its parents, as well as from all other varieties of which I am aware:

1. A profusion of glands on the stipules of the flowers (moss);
2. A profusion of thorns on the stems and peduncles;
3. Dark green, leathery, disease-resistant foliage; and
4. Bright yellow, ten-petalled flowers.
5. Produces hips freely, which turn brown and scaly at maturity and are covered with thorns.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—Unnamed seedling.

*Pollen parent.*—JACjel, U.S. Plant Pat. No. 4,438.

Classification:

*Botanical.*—*Rosa hybrida.*

*Commercial.*—Floribunda.

FLOWER

Observations made from specimens grown in a garden environment in Somis, Calif., from March through July, 1993.

Blooming habit: Recurrent.

Bud:

*Size.*—1 to 1¼ inches in length when the petals start to unfurl.

*Form.*—Long, pointed ovoid.

*Color.*—When sepals first divide, bud color is Yellow Group 13A. When half blown, the upper sides of the petals are Yellow Group 13A; and the lower sides of the petals are Yellow Group 13C.

*Sepals.*—Color: Green Group 138C. Surface texture: Covered in fine hairs. The outside of the sepal on a tight bud, before reflexing, is covered in aromatic glands, especially the appendaged sepals. There are three normal to heavily appendaged sepals. There are two unappendaged sepals with hairy edges.

*Receptacle.*—Color: Green Group 143A. Shape: Apple. Size. Small (¼ inch×¼ inch). Surface: Glandular, mossy and has prickles.

*Peduncle.*—Length: Short (2 to 2½ inches). Surface: Prickly and glandular. Color: Medium green. Strength: Stiff, erect.

Bloom:

*Size.*—Medium. Average open size is 3½ inches in diameter.

*Borne.*—Singly, several together in flat clusters of 3 to 5 flowers.

*Stems.*—Medium or short (8 to 12 inches) and strong.

*Form.*—When first open: High centered. Permanence: Flattens.

*Petalage.*—Number of petals under normal conditions: 10.

*Color.*—The upper and reverse sides of the petals are Yellow Group 13C. The base of each petal has a very small, Yellow Group 13A half moon at the point of attachment. The major color on the upper side is Yellow Group 13C.

*Variegations.*—None.

*Discoloration.*—The general tonality at the end of the first day: No change. By the end of the third day: A slight fading to Yellow Group 11A.

*Fragrance.*—Strong.

Petals:

*Texture.*—Thick.

*Shape.*—Round.

*Form.*—Flat.

*Arrangement.*—Imbricated, with few petaloids in the center.

*Persistence.*—Drop off cleanly.

*Lastingness.*—On the plant: Short (3 to 4 days). As a cut flower: Short (3 to 4 days).

Reproductive parts:

*Anthers.*—Size: Medium. Quantity: Many. Color: Yellow. Arrangement: Regular around the styles.

*Filaments.*—Color: Yellow.

*Pollen.*—Color: Gold-yellow.

*Styles.*—Color: Red.

*Stigmas.*—Color: Greenish-white.

Form: Bush.

Growth: Vigorous, upright, branching. Average height in California is 48 inches; spread is 36 inches.

Foliage:

*Number of leaflets on normal mid-stem leaves.*—5 or 7.

*Size.*—Large (6 inches$\times$4½ inches).

*Quantity.*—Normal.

*Color.*—New foliage: Greyed-Purple Group 183A. Old foliage: Green Group 139A.

Leaflets:

*Shape.*—Pointed oval.

*Texture.*—Upper side: Leathery and glossy.

*Edge.*—Serrated.

*Serration.*—Single and small.

*Petiole rachis.*—Color: Reddish when young, then green.

*Petiole underside.*—Rough with prickles.

*Stipules.*—Long (1 inch) and bearded.

*Disease resistance.*—Resistant to mildew and rust under normal growing conditions at Somis, Calif.

Wood:

*New wood.*—Color: Dark green. Bark: Smooth.

*Old wood.*—Color: Green. Bark: Smooth.

Prickles:

*Quantity.*—Many on main canes from base. Many on laterals from main canes.

*Form.*—Medium (¼ inch) and hooked downward.

*Color when young.*—Green.

Small prickles:

*Quantity.*—Many on main stalks. Many on laterals.

*Color.*—Green when young and then brown.

I claim:

1. A new and distinct variety of rose plant of the floribunda class, substantially as herein shown and described, characterized particularly as to novelty by the unique combination of its profusion of glands and thorns on stipules and peduncles; its profusion of thorns on stems; its dark green, leathery foliage; and its free production of hips that turn brown and scaly at maturity and are covered with thorns.

* * * * *

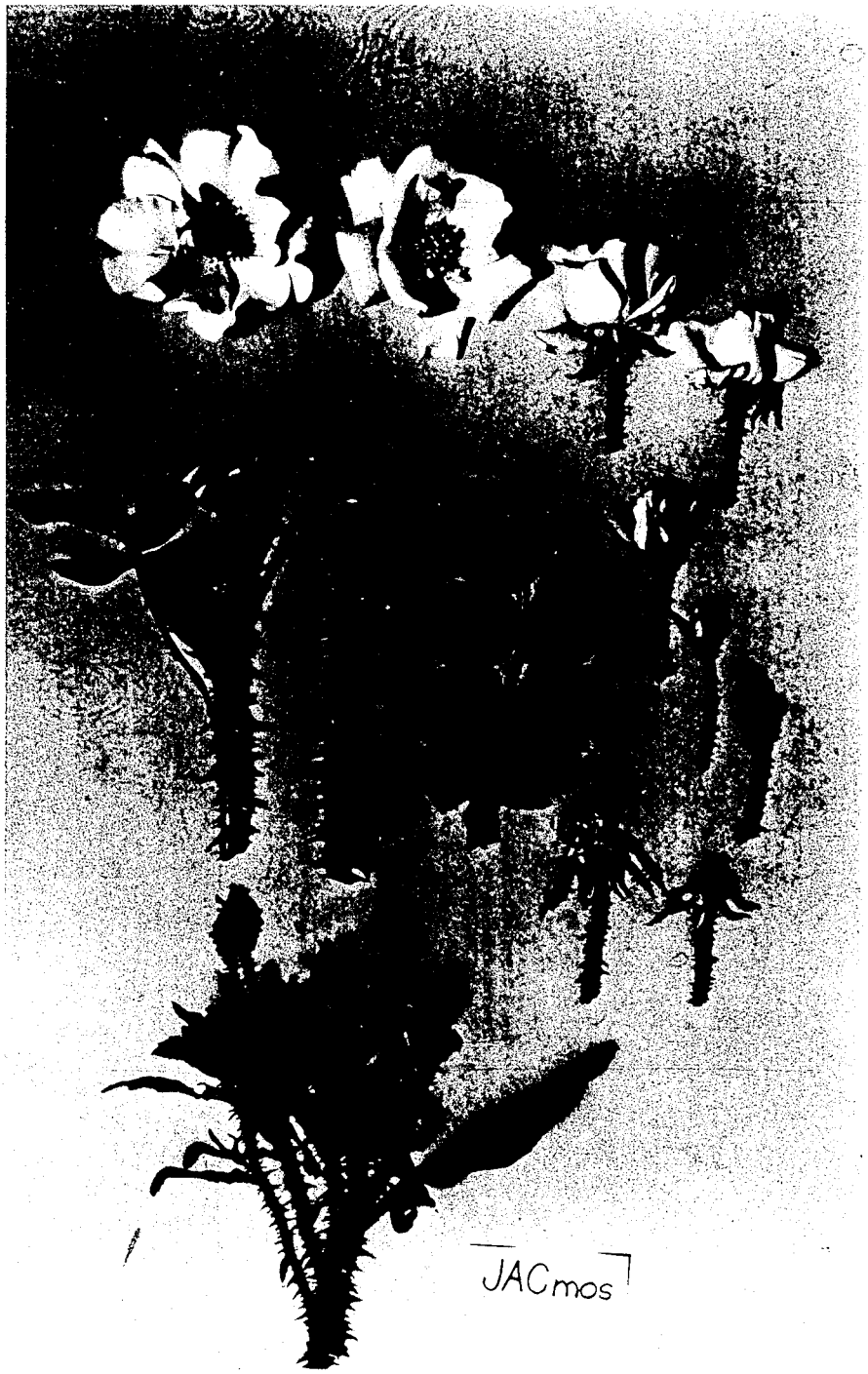
JACmos